United States Patent
Dauhajre et al.

(10) Patent No.: US 11,420,013 B2
(45) Date of Patent: Aug. 23, 2022

(54) VIBRATION SUPPRESSION APPARATUS

(71) Applicant: Kynetika, Inc., Seattle, WA (US)

(72) Inventors: Abraham A. Dauhajre, Coral Springs, FL (US); Abraham Alexander Dauhajre, Seattle, WA (US); Daniel P. Dauhajre, Santa Monica, CA (US); Michael Klasco, Richmond, CA (US)

(73) Assignee: Kynetika, Inc., Seattle, WA (US)

( * ) Notice: Subject to any disclaimer, the term of this patent is extended or adjusted under 35 U.S.C. 154(b) by 0 days.

(21) Appl. No.: 17/448,388

(22) Filed: Sep. 22, 2021

(65) Prior Publication Data
US 2022/0096787 A1   Mar. 31, 2022

Related U.S. Application Data

(60) Provisional application No. 63/084,559, filed on Sep. 28, 2020.

(51) Int. Cl.
*A61F 2/24* (2006.01)
*A61M 21/02* (2006.01)
(Continued)

(52) U.S. Cl.
CPC .............. *A61M 21/02* (2013.01); *A61F 2/24* (2013.01); *G01H 1/00* (2013.01);
(Continued)

(58) Field of Classification Search
CPC   G16H 15/00; A61B 5/6805; A61B 17/22004; A61B 5/7455;
(Continued)

(56) References Cited

U.S. PATENT DOCUMENTS

| 6,466,673 B1 | 10/2002 | Hardy |
| 7,974,689 B2 | 7/2011 | Volpe et al. |

(Continued)

FOREIGN PATENT DOCUMENTS

| CN | 104856718 A | 8/2015 |
| DE | 10250273 A1 | 5/2004 |
| KR | 101327694 B1 | 11/2013 |

OTHER PUBLICATIONS

Cardiac Valve Noise Reduction by Non-Drug Interventions Improves the Sleep Quality of Patients after Mechanical Cardiac Valve Implantation. Lin Y, Le X, Huang X, Jiang, F, Lin F, Ye Q, and Lin J. Ann Thorac Cardiovasc Surg 2016; 22:69-75. (Year: 2016).*

(Continued)

*Primary Examiner* — Christine H Matthews
*Assistant Examiner* — Joshua Daryl D Lannu
(74) *Attorney, Agent, or Firm* — MLO, a professional corp.

(57) ABSTRACT

Systems and methods for reducing vibrations perceived by a human due to an artificial heart valve include a vest that is wearable around a torso of the human, a plurality of sensors mounted to the vest, a plurality of vibration-generating actuators mounted to the vest, and a controller. The plurality of sensors detects vibrations in the human generated by the artificial heart valve. The controller is operable to receive signals representing the detected vibrations from the plurality of sensors, and is operable to produce anti-vibration signals that substantially attenuate the detected vibrations. A first sensor of the plurality of sensors is located near a first vibration-generating actuator of the plurality of vibration-generating actuators to form a sensor/actuator set. In the sensor/actuator set, the anti-vibration signals generated by the controller for the first vibration-generating actuator correspond to the vibrations detected by the first sensor.

14 Claims, 9 Drawing Sheets

(51) Int. Cl.
  *G01H 1/00* (2006.01)
  *A61M 21/00* (2006.01)
(52) U.S. Cl.
  CPC ............ *A61M 2021/0022* (2013.01); *A61M 2205/3375* (2013.01); *A61M 2209/088* (2013.01)
(58) Field of Classification Search
  CPC ............ A61B 2562/0219; A61B 5/349; A61B 2562/0204; A61B 5/0051; H04R 29/004; G01P 9/00; G01P 1/003; F16F 7/00; F16F 2224/00; F16F 2222/00; F16F 2230/00
  See application file for complete search history.

(56) References Cited

U.S. PATENT DOCUMENTS

| | | | |
|---|---|---|---|
| 2011/0319703 | A1 | 12/2011 | Wiskerke et al. |
| 2017/0020704 | A1* | 1/2017 | Wu ..................... A61B 5/4836 |
| 2018/0020969 | A1* | 1/2018 | Cinquin ............... A61B 5/0024 |
| | | | 600/595 |
| 2019/0343480 | A1* | 11/2019 | Shute ..................... A61B 5/349 |
| 2020/0068708 | A1* | 2/2020 | Longinotti-Buitoni ...................... |
| | | | A61B 5/7475 |

OTHER PUBLICATIONS

International Search Report and Written Opinion dated Dec. 21, 2021 for PCT Patent Application No. PCT/IB2021/058653.
Johansen, P et al., "A new method for quantitative evaluation of perceived sounds from mechanicalheart valve prostheses", Proceedings of the Institution of Mechanical Engineers, Jan. 1, 2000, vol. 214, part H, pp. 121-128. See abstract; and p. 122.
Sapsanis, Christos et al., "StethoVest: a simultaneous multichannel wearable system for cardiacacoustic mapping", 2018 IEEE Biomedical Circuits and Systems Conference (BioCAS), Oct. 17-19, 2018, pp. 1-4 (https://ieeexplore.ieee.org/document/8584742).
Altunkaya et al., "Comparison of first and second heart sounds after mechanical heart valve replacement," Computer Methods in Biomechanics and Biomedical Engineering, 16:4, Jan. 2012, Abstract Only.
Bai et al., The embedded digital stethoscope uses the adaptive noise cancellation filter and the type I Chebyshev IIR bandpass filter to reduce the noise of the heart sound, Proceedings of 7th International Workshop on Enterprise networking and Computing in Healthcare Industry, 2005, HEALTHCOM 2005, Jun. 2005, Abstract Only.
Blome-Eberwein et al., Impact of Mechanical Heart Valve Prosthesis Sound on Patients' Quality of Life, Ann Thorac Surg. vol. 61(2), Feb. 1996, pp. 594-602.
Gupta et al., Precision wearable accelerometer contact microphones for longitudinal monitoring of mechano-acoustic cardiopulmonary signals, npj Digital Medicine, 3, Article No. 19, Feb. 2020, 8 pages, https://www.nature.com/articles/s41746-020-0225-7.pdf.
Johansen et al., A new method for quantitative evaluation of perceived sounds from mechanical heart valve prostheses, Proceedings of the Institution of Mechanical Engineers, Part H: Journal of Engineering in Medicine, vol. 214 (1): 8—Jan. 1, 2000, 8 pages.
Lin et al., Cardiac Valve Noise Reduction by Non-Drug Interventions Improves the Sleep Quality of Patients after Mechanical Cardiac Valve Implantation, Annals of Thoracic Cardiovascular Surgery, vol. 22, Feb. 8, 2016, pp. 69-75.
Nielsen et al., Psychoacoustic Quantification of Mechanical Heart Valve Noise, J Heart Valve Dis. vol. 14(1), Jan. 2005, pp. 89-95.
Tang et al., Noise and Disturbance Reduction for Heart Sounds in Cycle-Frequency Domain Based on Nonlinear Time Scaling, IEEE Transactions on Biomedical Engineering, vol. 57, No. 2, Feb. 2010, pp. 325-333.

* cited by examiner

VIBRATION SUPPRESSION APPARATUS

RELATED APPLICATIONS

This application claims priority to U.S. Provisional Application No. 63/084,559, filed on Sep. 28, 2020, and entitled "Vibration Suppression Apparatus," which is hereby incorporated by reference in full.

BACKGROUND

Artificial internal devices in and/or around the heart, such as artificial heart valves, produce vibrations that propagate through the body's internal bone structure, tissue, etc. The fluttering (opening and closing) of the valves transmits vibrations through the body, and as these vibration waves propagate, they are felt by the patient.

The amplitude of these vibrations can be large enough that many patients suffer from sleep deprivation and other disorders due to these vibrations. In different body positions, the vibrations can be very uncomfortable, keeping patients awake at night. Studies of the impact of heart valve vibrations on the quality of life (QOL) of patients have shown that heart valve recipients can experience severe sleep disturbance, which can then lead to further health issues such as chronic stress. Some solutions to these sleep problems are directed at improving the design of mechanical heart valves. Other solutions involve therapies for the patient, including drug interventions such as administering sedatives, or non-drug interventions such as cognitive behavioral therapy and wearing noise-cancelling earplugs. However, the effect of mechanical heart vibrations on the quality of life of patients continues to be a significant ongoing problem.

SUMMARY

In embodiments, a system for reducing vibrations perceived by a human due to an artificial heart valve includes a vest that is wearable around a torso of the human, a plurality of sensors mounted to the vest, a plurality of vibration-generating actuators mounted to the vest, and a controller. The plurality of sensors detects vibrations in the human generated by the artificial heart valve. The controller is operable to receive signals representing the detected vibrations from the plurality of sensors, and is operable to produce anti-vibration signals that reduce the detected vibrations. A first sensor of the plurality of sensors is located near a first vibration-generating actuator of the plurality of vibration-generating actuators to form a sensor/actuator set. In the sensor/actuator set, the anti-vibration signals generated by the controller for the first vibration-generating actuator correspond to the vibrations detected by the first sensor.

In embodiments, an apparatus for reducing vibrations perceived by a human due to an artificial heart valve is a vest that is wearable around a torso of the human. A plurality of sensors is mounted to the vest, where the plurality of sensors detects vibrations in the human generated by the artificial heart valve. A plurality of vibration-generating actuators is mounted to the vest. A first sensor of the plurality of sensors is located near a first vibration-generating actuator of the plurality of vibration-generating actuators to form a sensor/actuator set.

In some embodiments, methods for reducing vibrations perceived by a human due to an artificial heart valve involve providing a setup vest that is wearable around a torso of the human. The setup vest has a first plurality of sensors and a first plurality of vibration-generating actuators that are repositionable on the setup vest. A calibration session is conducted to customize a placement of the first plurality of sensors and the first plurality of vibration-generating actuators on the setup vest. A vest is provided to the human, the vest having a second plurality of sensors and a second plurality of vibration-generating actuators mounted on the vest according to the placement from the calibration session. At least one sensor of the second plurality of sensors is located near at least one vibration-generating actuator of the second plurality of vibration-generating actuators to form a sensor/actuator set.

DETAILED DESCRIPTION

Figure 1:
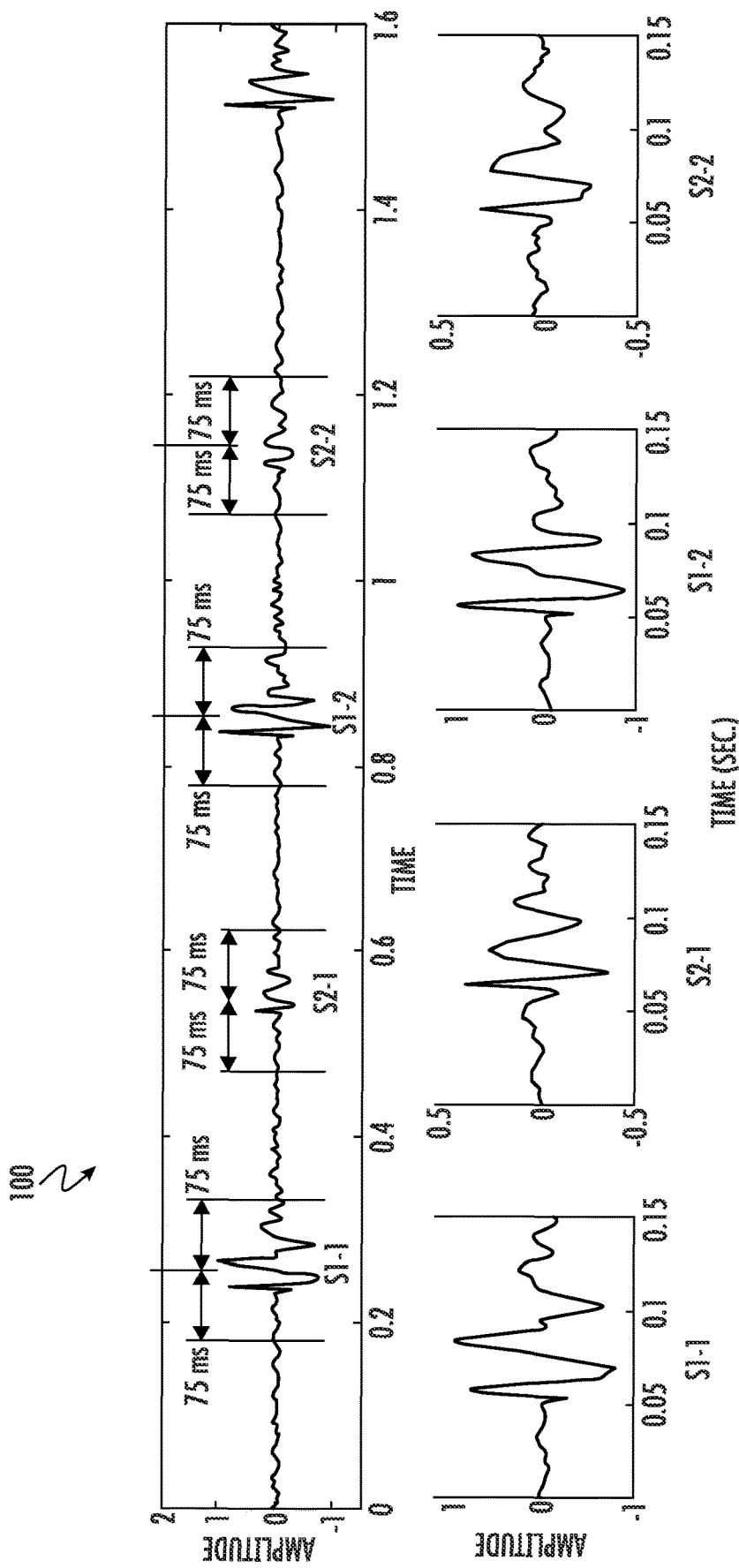
FIG. 1 is an example of a phonocardiogram as known in the art.

Many people suffer from heart or heart valve problems that result in surgery and replacement of the natural aortic or mitral valves. There are several types of artificial heart valves; some are mechanical while others are made of tissue (human donor or animal tissue). However, all of these artificial valves, whether mechanical or tissue valves, generate undesirable vibrations throughout the chest cavity as the heart pumps. These vibrations propagate through the bone structure and the tissue of the chest.

Systems and methods of the present disclosure involve a vibration suppression device worn externally on a person's torso to significantly attenuate the vibrations perceived by the patient due to an artificial heart valve. The vibrations may include tactile sensations felt by the patient as well as audible noise heard by the patient. The vibration suppression device is in the form of a chest covering worn by the patient that has sensors located around the patient's torso. The chest covering may be in the form of, for example, a vest. The sensors in the vest read the vibrations on the outside of the chest that are generated by the heart valves. In some embodiments, sensors are co-located with vibration-generating actuators in sets so that anti-vibration signals for a particular actuator is based on signals sensed by the sensor it is paired with. These sensor/actuator sets advantageously provide more accurate noise cancellation as compared to a single noise cancellation generated for the overall system. Such noises may include audible and/or inaudible signals. The sensors and actuators may be placed in locations on the vest that are customized for the individual patient.

In some embodiments, the vibration suppression systems of the present disclosure uniquely learn the heart valve vibration characteristics of an individual person and customize vibration cancelling signals to significantly reduce the effects of those vibrations. Such systems include electronics and microcontrollers that use real-time data from the sensors along with a specially designed adaptive software algorithm to predict the next vibration pulse. The electronics drive vibration-generating actuators, which are also located on the vest, to counter the vibrations coming from the artificial heart valves internally within the patient. The system senses, learns, adapts, predicts, and generates anti-vibration pulses so that the perceived internal vibrations are significantly attenuated. Uniquely designed signal cancelation methods are utilized to algorithmically calibrate the sensors to each patient to account for inter-patient variability.

In this disclosure, vibration suppression may be referred to as anti-vibration, vibration cancellation, noise cancellation, or noise suppression. Signals generated by vibration-generating actuators may be referred to as vibrations, pulses, or waves. Vibration suppression shall refer to decreasing the vibrations perceived the patient, such as substantially or significantly reducing, attenuating, cancelling, or eliminating the vibrations to a level that is acceptable to the patient.

FIG. 1 shows a typical phonocardiogram 100 of heart sounds, measured by a sensing device on the chest. The heart sounds typically include at least two pulses—S1 caused by the mitral and tricuspid valves closing at the beginning of systole, and S2 caused the aortic and pulmonary valves closing at the end of systole. Two cycles of each are shown in FIG. 1, labeled as S1-1, S2-1, S1-2, and S2-2, with close-up views of each also being shown. Artificial valves generate pulses similar to those seen in FIG. 1. As vibrations generated by artificial valves travel through the chest cavity, they are picked up by nerve endings and are then felt by the patient which can in many cases result in anxiety and loss of sleep. The vibrations generated by artificial valves can exhibit variability from patient to patient, such as in waveform, frequency and/or amplitude. The variability is a function of each patient's internal bone and tissue structures, density, and other factors, thus making the vibrations difficult to characterize in a universal manner. Additionally, the vibrations can vary in an individual during the course of a day such as due to physical exercise, stress, or sleeping. The vibrations can also change over time for an individual such as due to aging, weight loss or gain, or changes in health conditions. Thus, heart sounds in humans are very complex to characterize.

Figure 2:
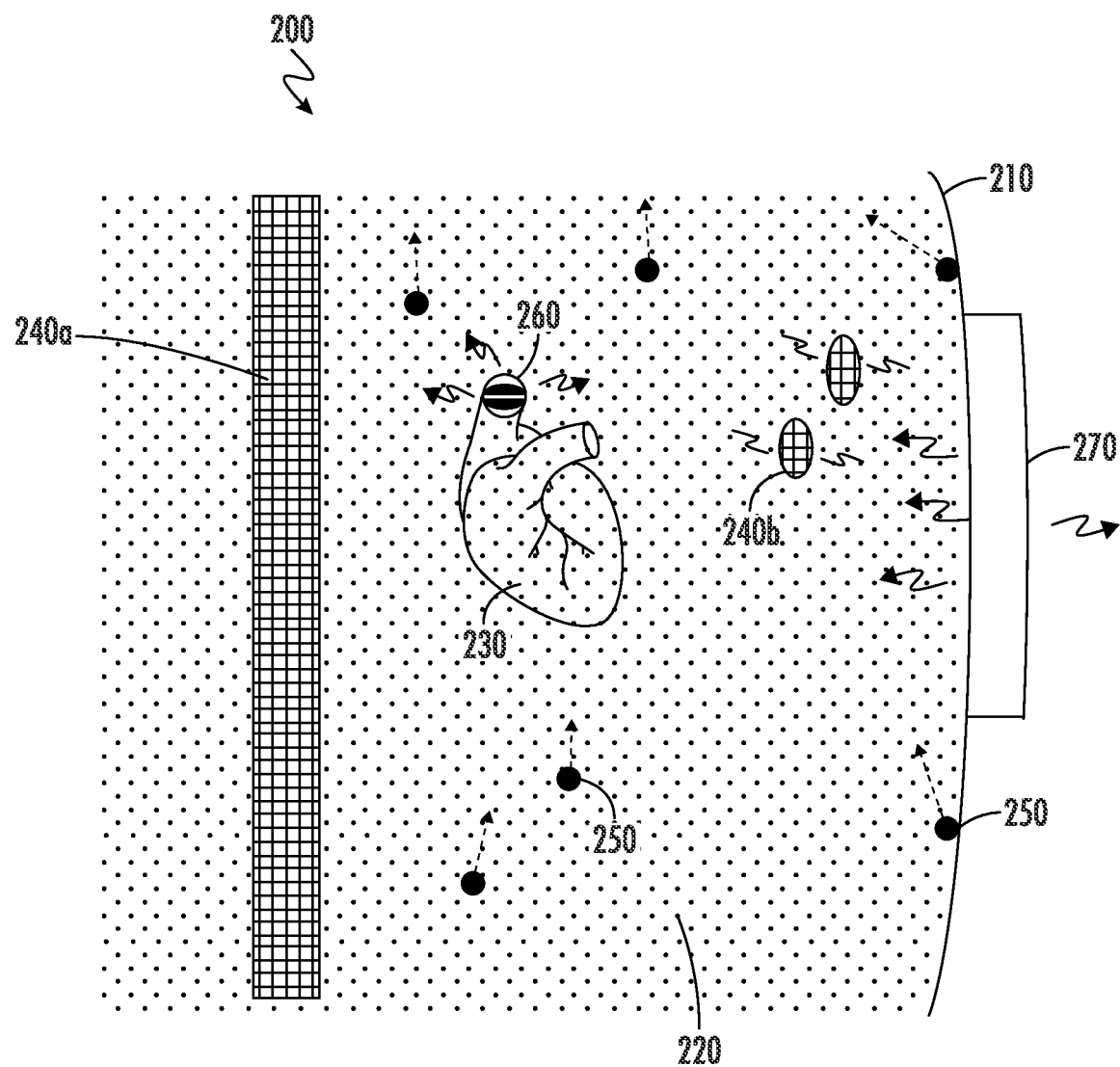
FIG. 2 is a cross-sectional schematic side view of a human chest with a vibration suppression apparatus, in accordance with some embodiments.

FIG. 2 is a cross-sectional schematic of a human torso 200, illustrating anatomical aspects that vary from individual to individual and that affect the generation and transmission of vibration signals within the human body. Illustrated in FIG. 2 are skin 210, soft tissue 220, a heart 230, bones 240*a* and 240*b*, and nerve endings 250. Bone 240*a* is shown in a longitudinal view, such as representing a spine, while bones 240*b* are shown in cross-section, such as ribs. The size, location, density, and other aspects of these anatomical features will vary between patients, resulting in complexities for generating noise-cancelling signals that cannot be addressed using conventional techniques. For example, the weight, body mass and muscle tone of a patient will affect how the vibrations propagate through their chest cavity.

The initial source of noise vibrations to be addressed in the present disclosure is an artificial heart valve 260. Even if the same type of valve is implanted in two different patients, the generated vibrations will differ between the two patients based on their individual physiology. The transmission of the vibrations through the body will also differ between those two patients. The noise vibrations travel through soft tissue 220 (muscles, fat, etc.) to bones 240*a,b* and skin 210. Nerve endings 250 in many places in the body pick up the vibrations and send signals to the brain. Depending on the position of bones within the soft tissue, the type of soft tissues that are present (e.g., ratio of muscle to fat), and the location and amount of nerve endings, the vibrations will be perceived differently in different patients. To address these vibration sounds and physical sensations, the present disclosure describes a vibration suppression device 270 that is worn on a chest of the patient. The vibration suppression device 270 senses and analyzes heart sounds generated by the patient, and analyzes and produces anti-vibration signals to significantly reduce the artificial heart valve sounds perceived by the patient. The vibration suppression apparatus 270 advantageously accommodates people of different anatomies by enabling customization of sensor placements in the vest. The apparatus 270 also continuously monitors and adapts to the patient's heart signals, such as by using an algorithm to predictively analyze and produce anti-vibration signals.

Systems shall be described primarily in the form of a vest worn on the chest of a human, such as underneath their clothes to have direct contact with the skin. However, the wearable apparatuses of the present disclosure may be configured in other forms such as a band, belt or strip that covers at least a portion of the chest over the region of the heart. Embodiments referring to a "vest" in this disclosure shall apply to these other configurations as well.

Figure 3A:
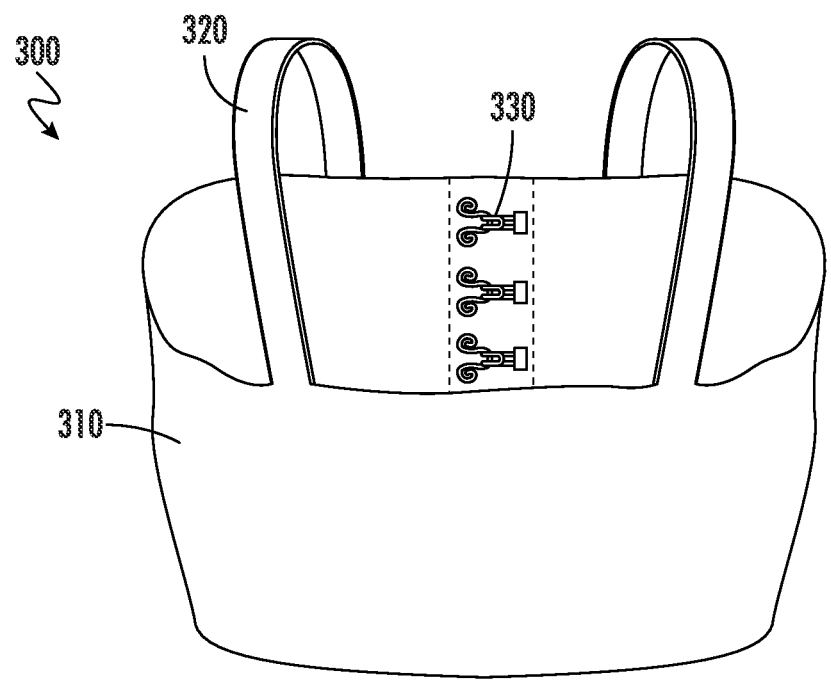
FIG. 3A shows an isometric view of a vibration suppression apparatus, in accordance with some embodiments.
Figure 3B:
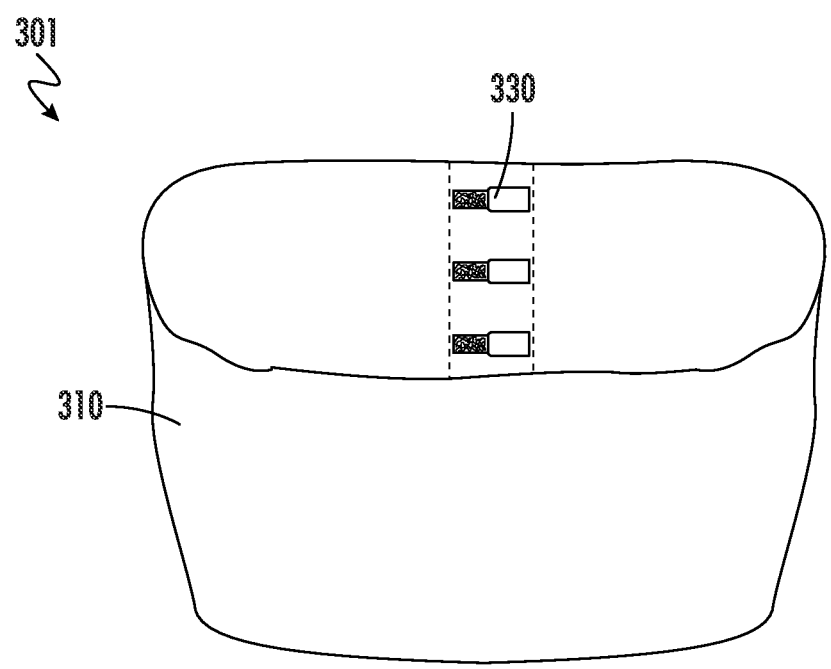
FIG. 3B shows an isometric view of another vibration suppression apparatus, in accordance with some embodiments.

FIG. 3A shows an example of a vest 300 in accordance with some embodiments, which contains components of the vibration suppression system. The vest 300 has a main portion 310 that covers at least a region over the patient's heart. For example, the main portion 310 may cover at least the pectoral region, or the rib cage, or may cover the entire torso such as from the shoulders to the waist. The vest 300 includes shoulder straps 320 in this example, to help prevent the vest 300 from sliding down on the patient. However, in other embodiments the straps 320 need not be included such that the apparatus includes only the main portion 310, as shown by the chest band 301 in FIG. 3B. The vest 300 may be offered in different versions for men and women, such as having different size ranges, contours, or styles (e.g., wider straps 320 for men versus women). The vest 300 and chest band 301 have adjustment mechanisms 330 to make the size adjustable for securing around a patient's torso. The adjustment mechanism 330 is positioned on the user's back. The adjustment mechanism 330 is illustrated as hook and eye closures in FIG. 3A and as hook-and-loop fasteners in FIG. 3B. In other embodiments adjustment mechanism 330 may be, for example, buckles, buttons, straps with slides/adjusters, and/or other means. The main portion 310 is made of a soft material that is comfortable for the wearer, such as natural or synthetic fabrics. In some embodiments, the material may be an elastic fabric to allow for stretching and contraction as the user's chest expands and contracts. In some embodiments, the material of the main portion 310 may be selected to be a material that substantially isolates the anti-vibration signals from spreading laterally along the vest 300 or chest band 301.

Figure 4A:
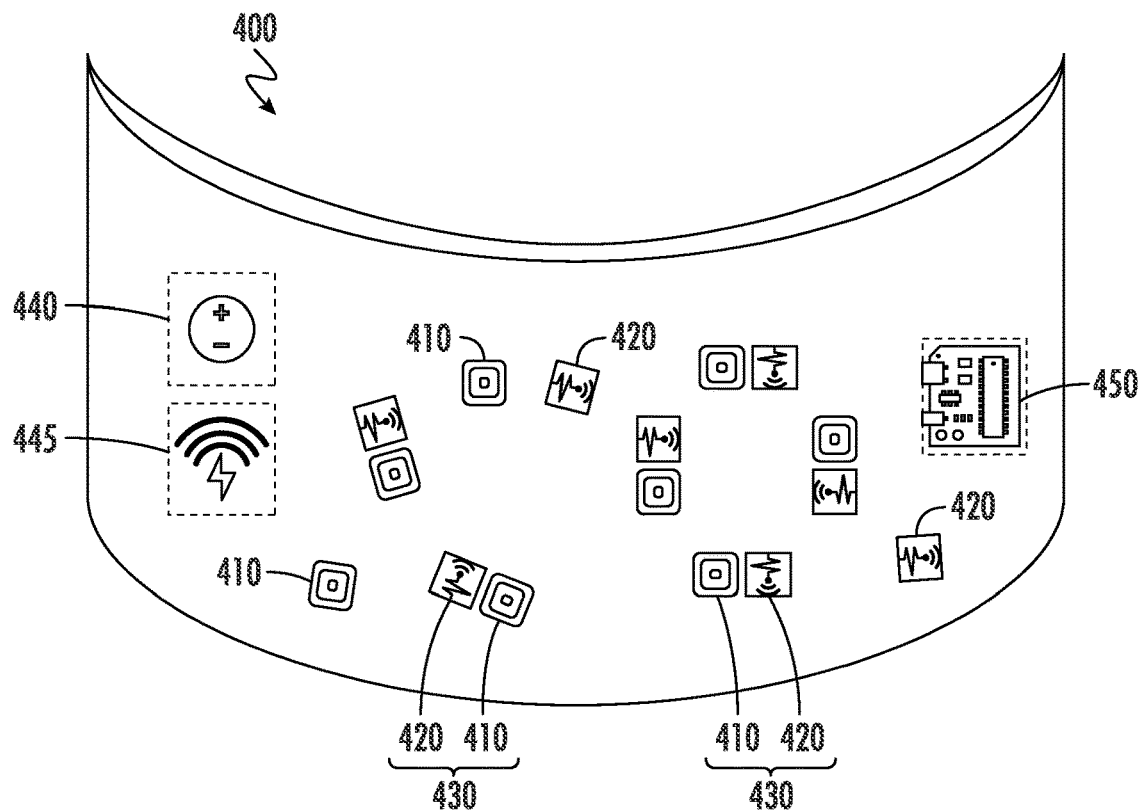
FIG. 4A is a diagram of a vibration suppression apparatus, in accordance with some embodiments.

FIG. 4A is a schematic showing example placements of components in the main portion of a vest 400, in accordance with embodiments. Only the front section of the vest 400 is shown for simplicity. A plurality of sensors 410 and vibration-generating actuators 420 are positioned at various locations along the vest 400, to address heart sound signals across the user's chest. The vibration-generating actuators 420 produce anti-vibration signals; that is, vibrations that attenuate or reduce the artificial heart valve noises perceived by the patient. Using multiple sensors 410 and actuators 420 in the system (e.g., at least two sensors and at least two vibration-generating actuators) improves the accuracy and sensitivity of detecting signals and enables more complete attenuation of vibrations as compared to using a single sensor and actuator.

One or more sensors 410 can be located near each vibration-generating actuator 420 that work together to form a sensor/actuator set 430. In these sensor/actuator sets 430, each vibration-generating actuator 420 can generate an attenuation signal that corresponds to the vibrations sensed by the sensor 410 near its location. That is, a first sensor 410 of the plurality of sensors may be located near a first vibration-generating actuator 420 of the plurality of vibration-generating actuators to form a sensor/actuator set 430. In the sensor/actuator set 430, the anti-vibration signals generated by the system (e.g., a controller) for the first vibration-generating actuator correspond to vibrations detected by the first sensor. For example, a controller that receives and sends data to/from the sensors and actuators may be instructed or programmed to associate the sensor(s) and actuator(s) of a set with each other. A sensor/actuator set 430, may comprise, for example one sensor 410 and one actuator 420, or one or more sensors 410 with one or more actuators 420. In some embodiments, two or more sensors 410 are placed with a separation distance from each other such that a gradient in amplitude of the vibrations sensed by the two or more sensors 410 may be determined. In one example using piezoelectric-type sensors and vibration-generating actuators, the sensors 410 and actuators 420 are each approximately ½-inch square and are placed next to or in close proximity with each other.

Having sensor/actuator sets in which anti-vibration actuators generate signals according to vibrations sensed near their location is beneficial because vibrations will vary in direction relative to the heart. The sensor/actuator sets 430 in accordance with some embodiments advantageously enable actuators 420 to specifically target the vibrations sensed at that particular location. The sensor/actuator sets 430 are distributed across the patient's chest, where the number of sensor/actuator sets 430 and the spacing between them may be determined by factors such as bone density, rib structure, and/or body fat percentage. For example, a heavier individual or an individual with higher fat percentage may require more sensors and/or smaller spacing between sensors than leaner individuals or those with lower fat percentage. In another example, women's vests may be designed with sensor spacings and locations that are different from men's vests, to accommodate for the anatomical differences between women and men in the chest area. As demonstrated in FIG. 4A, the sensor/actuator sets 430 may be arranged in various orientations, spacings, and arrangements relative to each other depending on the noise disturbances assessed for the particular patient. FIG. 4A also illustrates that some sensors 410 and actuators 420 may be located separately from each other (i.e., not in sets), such as to provide additional sensing data or to provide anti-vibration signals based on multiple sensors from different locations.

Figure 4B:
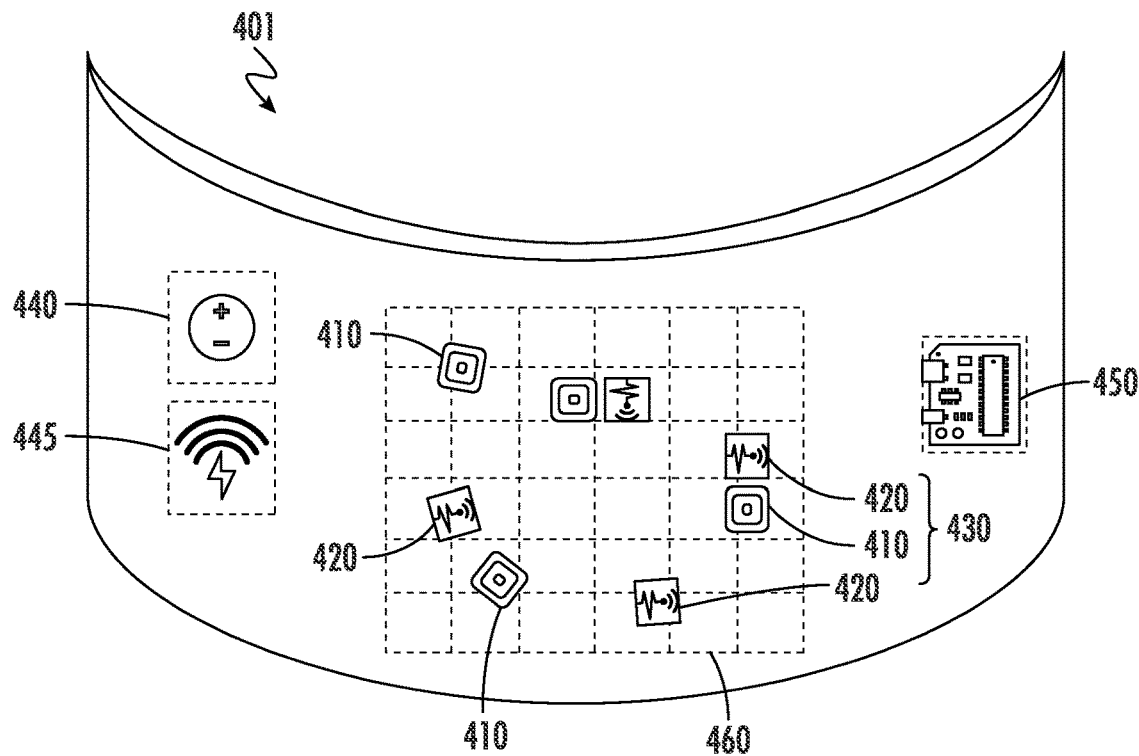
FIG. 4B is a diagram of a setup vest, in accordance with some embodiments.

FIG. 4B shows an embodiment of a main portion of a "setup" vest 401 for customizing the placement of sensors and actuators on an individual patient. The vest 401 includes adjustable features (e.g., adjustment mechanisms 330 of FIGS. 3A-3B) to fit the vest size snugly on the patient, so that vibrations can be properly sensed from and transmitted to the patient. Vest 401 has a test surface 460 for attaching and determining optimal placement locations for sensors 410 and actuators 420 during a setup session (which may also be referred to in this disclosure as a calibration session or calibration phase). The test surface 460 may include multiple connection locations for sensors and actuators to be releasably mounted to the vest. In some embodiments, the test surface may include a flexible circuit board and/or a wiring harness. The test surface 460 may be located on the inner surface of the vest 401, facing the patient, to have direct contact with the patient's body. Test surface 460 may be configured as a sheet over the working area of the vest 401, or as strips or pieces smaller than the full working area and placed in different regions of the vest.

The test surface 460 and/or the vest material may be configured with, for example, fasteners (e.g., hooks, clips, adhesive strips) to which the sensors 410, actuators 420 and/or sensor/actuator sets 430 are attached. Embodiments may also include compartments in which the sensor/actuator sets 430 can be held. The fasteners and/or compartments enable the sensors and actuators to be repositioned on the setup vest, to customize placement for the particular individual. In some embodiments, the test surface 460 may include location markings—shown as a grid in FIG. 4B—printed or drawn on the test surface 460 to serve as reference points for test locations of the sensors 410 and actuators 420 (e.g., individually or paired as sensor/actuator sets 430).

During the setup session, the sensors 410 and actuators 420 can be moved, reoriented, and otherwise repositioned and adjusted to determine the locations where the patient is experiencing heart valve signals having a highest signal amplitude. In some examples, the heart valve signals include audible and/or inaudible signals (e.g., vibrations and/or noise). The number and types of sensors and actuators can be varied during the setup session to achieve noise reduction results that are acceptable to the patient. In some embodiments, two or more of the sensors 410 are operable to provide an amplitude gradient of heart valve signals in order to quickly determine where the patient is experiencing heart valve signals having a highest signal amplitude. In some embodiments, a gradient of heart valve signals in a particular area can be measured by using multiple sensors that are temporarily placed in that area, to guide what direction to move the sensors for obtaining a better signal. Once an acceptable placement of the sensors and actuators has been achieved with the setup vest, a customized vest for that patient can be made with sensors and actuators mounted to the vest in the positions determined during the calibration session.

Also shown in FIGS. 4A and 4B are a battery 440 (e.g., a thin lithium-ion coin cell) to supply power for sensors 410, vibration-generating actuators 420 and electronics 450 that process signals to and from sensors 410 and vibration-generating actuators 420. In some embodiments, a wireless charger 445 is used to charge the battery 440. In some embodiments, the electronics 450 may be housed on a flexible electronic board in order to be comfortable for the wearer. In other embodiments, the electronics 450 and/or the battery 440 may be in power and signal communication with the sensors 410 and the vibration-generating actuators 420 but may be not mechanically fixed to the vest.

Embodiments may include minimizing the size of battery 440 for user comfort. The battery size may be minimized by, for example, providing a power saving mode for saving battery usage, and/or making the electronics 450 low power to provide longer battery life. The power saving mode may involve taking measurements less frequently if the sensor readings have not changed significantly in a certain period of time (e.g., if the patient is sedentary), or operating certain sensors and vibration-generating actuators at a less frequent measurement rate or actuation rate in regions where heart sound disturbances are not as prominent as in other regions. In some embodiments, the system may have a sleep mode for when the patient is asleep, in which a level of attenuation that is comfortable for the user is maintained by the microcontroller, but since the patient is asleep and not performing physical activities, ongoing monitoring and calculations of future heart sounds is not performed (thus saving battery life). In one embodiment, the system may be programmed to change to the sleep mode at a certain time of night. In another embodiment, the system may be in communication with an external monitor (e.g., the patient's smart watch or sleep monitor) that detects when the patient falls asleep and then instructs the vibration suppression system to switch to the sleep mode.

In embodiments, an apparatus for reducing vibrations perceived by a human due to an artificial heart valve is a vest that is wearable around a torso of the human. A plurality of sensors is mounted to the vest, where the plurality of sensors detects vibrations in the human generated by the artificial heart valve. A plurality of vibration-generating actuators is mounted to the vest. A first sensor of the plurality of sensors is located near a first vibration-generating actuator of the plurality of vibration-generating actuators to form a sensor/actuator set.

Figure 5:
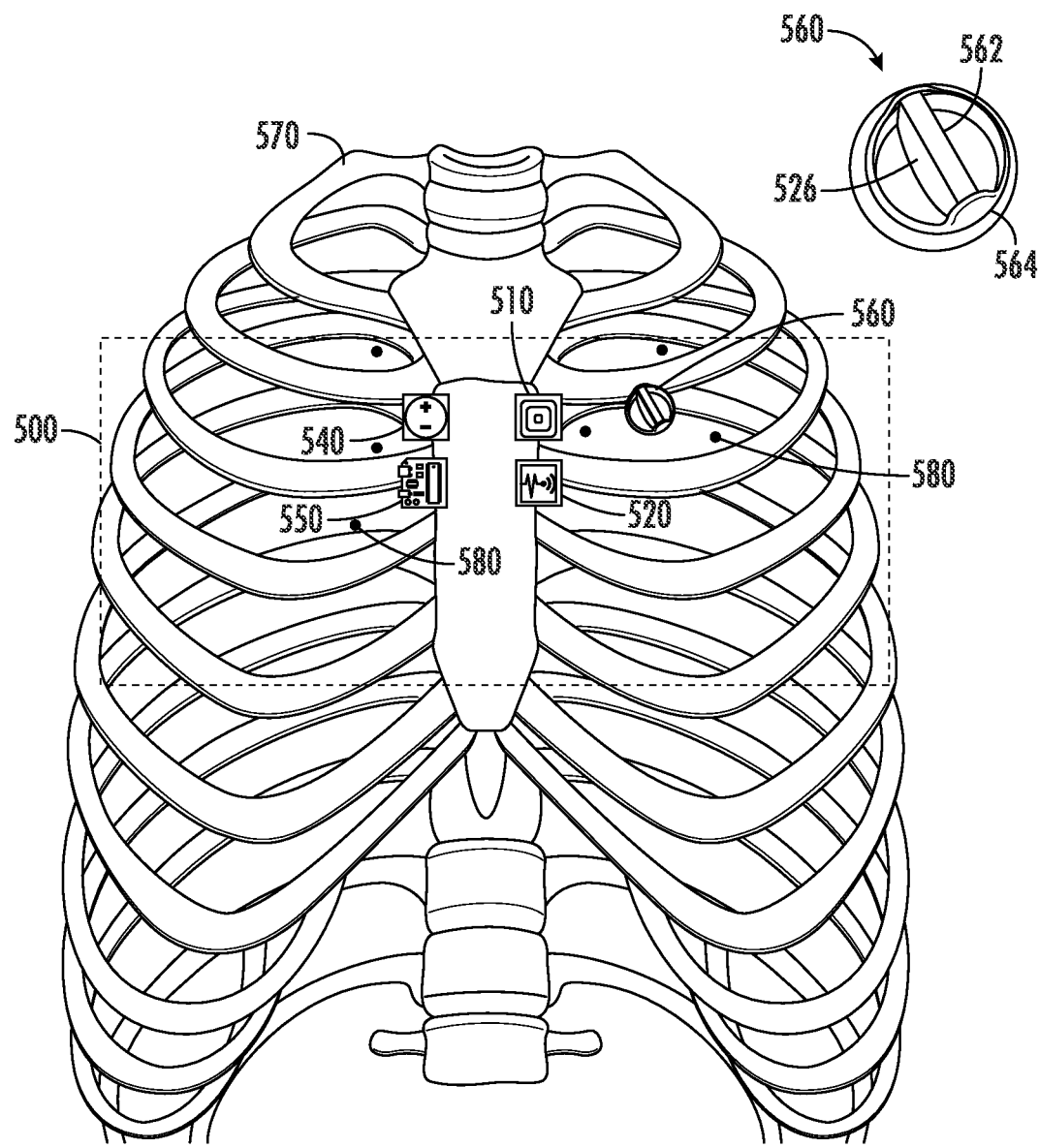
FIG. 5 is a schematic of a vibration suppression system on a human, in accordance with some embodiments.

FIG. 5 shows a block diagram of an apparatus 500 for suppression of vibrations produced by artificial internal devices inside a patient's body, in accordance with some embodiments. The apparatus 500 is a chest covering such as a vest worn by the user. Apparatus 500 includes vibration sensors 510 to detect vibrations resulting from the internal artificial devices (illustrated here as mechanical aortic valve 560), and vibration-generating actuators 520 to generate vibration cancelling waves. The apparatus 500 also includes a wireless rechargeable battery system 540 and electronics 550. Electronics 550 can include, for example, a microcontroller, an analog-to-digital converter, a digital-to-analog converter, BLUETOOTH® and Wi-Fi connectivity, amplifiers and memory.

In FIG. 5, as the heart pumps and activates the aortic valve 560, movement of the valve flaps 562 produces vibrations. The vibrations are transmitted through the valve body 564, then through the bone structure 570 of the patient and the tissue of the chest cavity. These vibrations are picked up by the many nerve endings 580, and the vibration sensation is then transmitted to the patient's brain. Using the vibration suppression apparatus 500 of the present disclosure, several vibration sensors 510 placed externally at several locations on the chest also pick-up these vibrations. Actuators 520 generate signals to reduce the vibrations perceived the patient, thereby improving comfort and quality of life.

Figure 6:
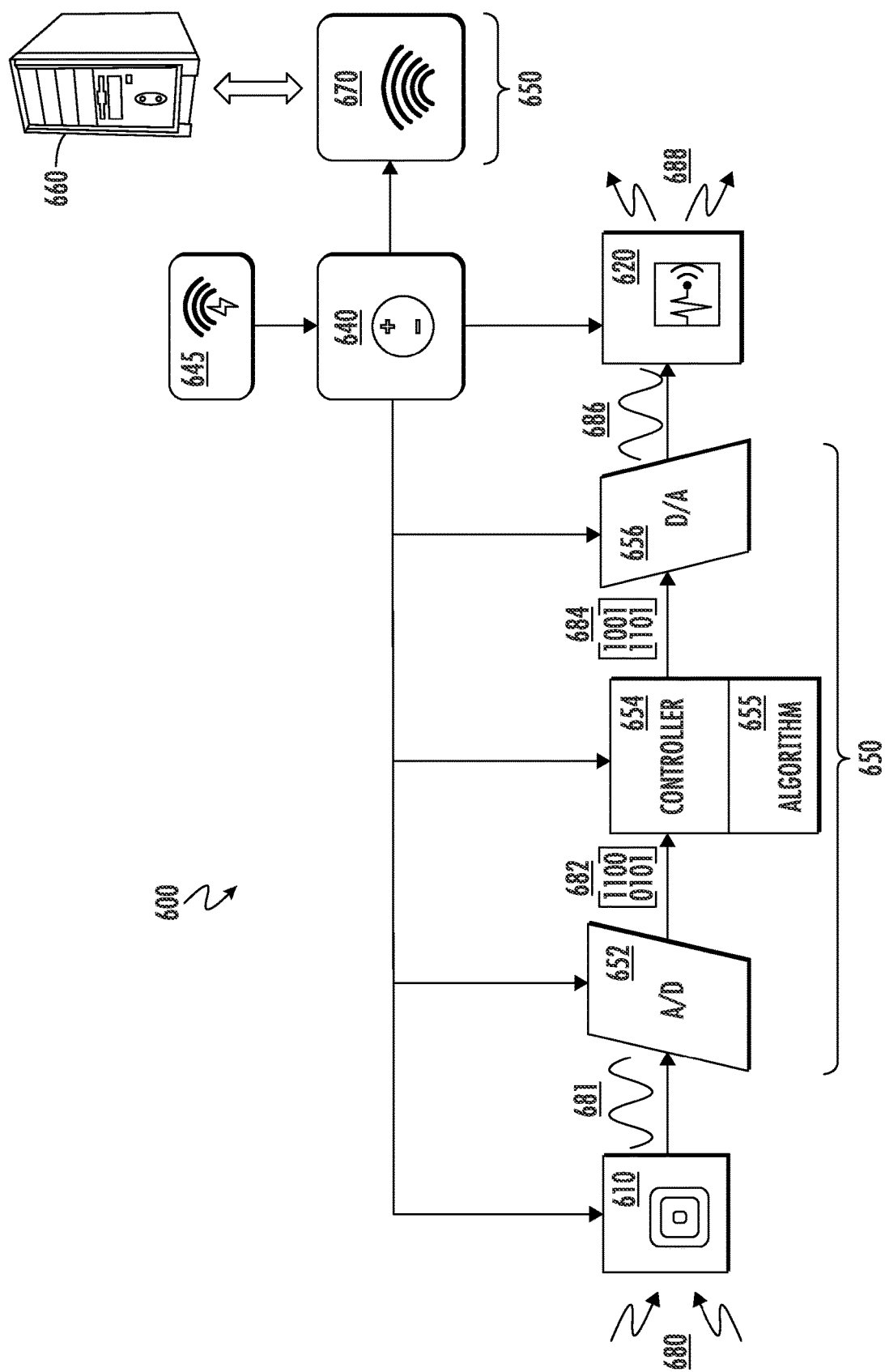
FIG. 6 is an electronic component block diagram of a vibration suppression system, in accordance with some embodiments.

FIG. 6 is a block diagram of a vibration suppression system 600, in accordance with some embodiments. The system includes an apparatus such as a vest or other chest covering worn by the patient, where the wearable apparatus includes vibration sensors 610, vibration-generating actuators 620, battery 640, battery charger 645 (e.g., a wireless charger), and electronics 650. The vibration-generating actuators 620 produce anti-vibration signals to attenuate or reduce the artificial heart valve noises perceived by the patient. The electronics 650 includes an analog-to-digital converter 652, a controller 654 (e.g., a microcontroller), and a digital-to-analog converter 656. Electronics 650 may also include a wireless transmitting system 670 on the same or separate circuit board as the other electronics. In some embodiments, the vibration suppression system 600 is in communication with a computing device 660, such as an external computer server or a cloud-based computing system.

Wireless transmitting system 670 is used to transmit and receive stored and real-time data via Bluetooth or Wi-Fi from vibration sensors 610, controller 654 and vibration-generating actuators 620 to computing device 660. The data may be gathered during an initial patient calibration phase and/or from ongoing monitoring of the patient to inform readjustments of parameters in algorithm 655 which may be, for example, a learning-adaptive-predictive (LAP) algorithm. Example parameters that may be learned by the algorithm 655 include characteristics of the heart pulses (e.g., waveform shape, time gap between S1 and S2, amplitude of S1 and S2, spectral (frequency spectrum) content of S1 and S2 pulses) and weighting of those characteristics.

Rechargeable battery 640 powers the components in the wearable vest. In some embodiments, battery charger 645 recharges the battery 640 wirelessly. In some embodiments, the battery charger 645 may include a physical connector to recharge the battery 640 via a plug-in charger. Information regarding battery charge level and/or system status may be provided to the patient via a cell-phone application or computer.

During usage, heart sounds and vibrations 680 are detected by vibration sensor 610 in the chest vest. Analog signals 681 from the vibration sensor 610 are transmitted to the analog-to-digital converter 652 which then sends digital data 682 to the controller 654. The digital data 682 is analyzed in real time by the controller 654, and the algorithm 655 in controller 654 generates an anti-vibration digital sequence 684. The controller 654 is operable to receive signals representing the detected vibrations from the plurality of sensors, and is operable to produce anti-vibration signals that substantially attenuate the detected vibrations. In some embodiments, algorithm 655 is a LAP algorithm that predicts the next vibrations that will be experienced by the patient and generates the anti-vibration digital sequence 684 to attenuate those signals. Aspects of the predicted vibrations can include the waveform, frequency, amplitude, pulse duration, time between pulses, and/or delay of occurrence of the pulses. The anti-vibration digital sequence 684 is optionally converted to an analog signal 686 via digital-to-analog converter 656. The anti-vibration analog signal 686 or the anti-vibration digital sequence 684 is applied to drive the vibration-generating actuators 620, which generate vibration cancelling anti-vibration signals 688 to the chest and/or other directions as needed.

The sensors 610 are operable to detect a mechanical vibration and/or an audible noise and provide a signal representative thereof to the analog-to-digital converter 652. The sensors 610 may include, but are not limited to, electrocardiography (ECG) sensors, piezoelectric sensors, micro-electromechanical (MEMS), accelerometers, dis-placement sensors, velocity sensors, pressure sensors and/or microphones. The vibration-generating actuators 620 are operable to receive a digital or analog signal and produce a mechanical vibration corresponding to the received signal. The vibration-generating actuators 620 may include, but are not limited to, haptic actuators (e.g., piezoelectric actuators, linear resonant actuators, and eccentric rotating mass actuators) and/or non-haptic actuators such as speakers or microphones.

The sensors 610 and vibration-generating actuators 620 may all be the same type and/or size throughout the vest or may be a variety of types and/or sizes. Because vibrations propagate in all directions, using different types and/or locations of sensors and vibration-generating actuators in the chest belt may more effectively cancel vibrations felt by the patient compared to a single sensor and actuator.

Sensors 610 may be utilized for detecting acoustic-airborne, audible clicking sounds heard by the patient (or people near the patient) as well as the haptic vibrations felt by the patient. Types of sensors for sensing acoustic sounds include microphones such as contact microphones (e.g., piezo-based) and micro-electromechanical (MEMS) microphones. In some embodiments, the sensors may be configured to detect frequencies in the audible range of humans (e.g., 20 Hz to 20 kHz) as well as below that range. For example, the sensors may include microphones that respond in the sub-audio (i.e., infrasonic) range, below 20 Hz. Although patients may not hear the infrasonic sounds, the information may help the LAP algorithm in predicting future vibrations. Types of sensors for picking up physical vibrations include accelerometers, such as three-axis accelerometers and piezoelectric MEMS accelerometers. Readings from the acoustic sensors and haptic vibration sensors may be used in correlation with each other to enhance identification of noise signals. For instance, the loudness of the audible heart valve clicks may be less than other sounds present, and thus the haptic vibration readings can be used to verify which signals detected by the acoustic sensors are due to the heart valve.

Sensors 610 are also chosen to have low latency, with response rates faster than the heart noise frequencies of interest. Sensors are chosen with an adequate acoustic overload point (AOP), so that the amplitude of signals that can be sensed by the sensor will not overload the microphones.

Various actuators 620 may be utilized to address both vibration noises perceived through the patient's hearing as well as tactile sensations felt by the patient by being transferred through their body (e.g., bones, soft tissue). In some embodiments, the actuators 620 and sensors 610 may be used as part of a feedforward or feedback vibration and/or audible noise cancellation topology. In an example of speakers being used as actuators in a feedforward topology, such speakers may face outward from the patient to cancel the audible heart valve clicking noises emanating from the patient's body. A sensor, e.g., a microphone, for picking up the audible clicking noise from the artificial heart valves may be paired with the speaker serving as an anti-vibration actuator, where the microphone is positioned such that it detects the audible sound leaving the vest. In contrast, the sensors 610 (e.g., microphones) and actuators 620 may be placed as close to the noise/vibration source as possible, such as next to the patient's skin at the location on the vest where the particular sensor is picking up the sound that is to be cancelled. The feedback speaker generates sound into the body, to cancel the vibrations from the source (heart valve).

In some embodiments, a plurality of sensors and a plurality of vibration-generating actuators are releasably mounted to the vest, thereby enabling positions of the plurality of sensors and the plurality of vibration-generating actuators to be adjusted. In some embodiments, the plurality of sensors and the plurality of vibration-generating actuators are mounted in locations customized to an individual patient. The plurality of sensors may include an accelerometer, a microphone, an acoustic sensor and/or a haptic vibration sensor. The plurality of vibration-generating actuators may include a haptic actuator, or a non-haptic actuator such as a feedforward microphone.

Figure 7:
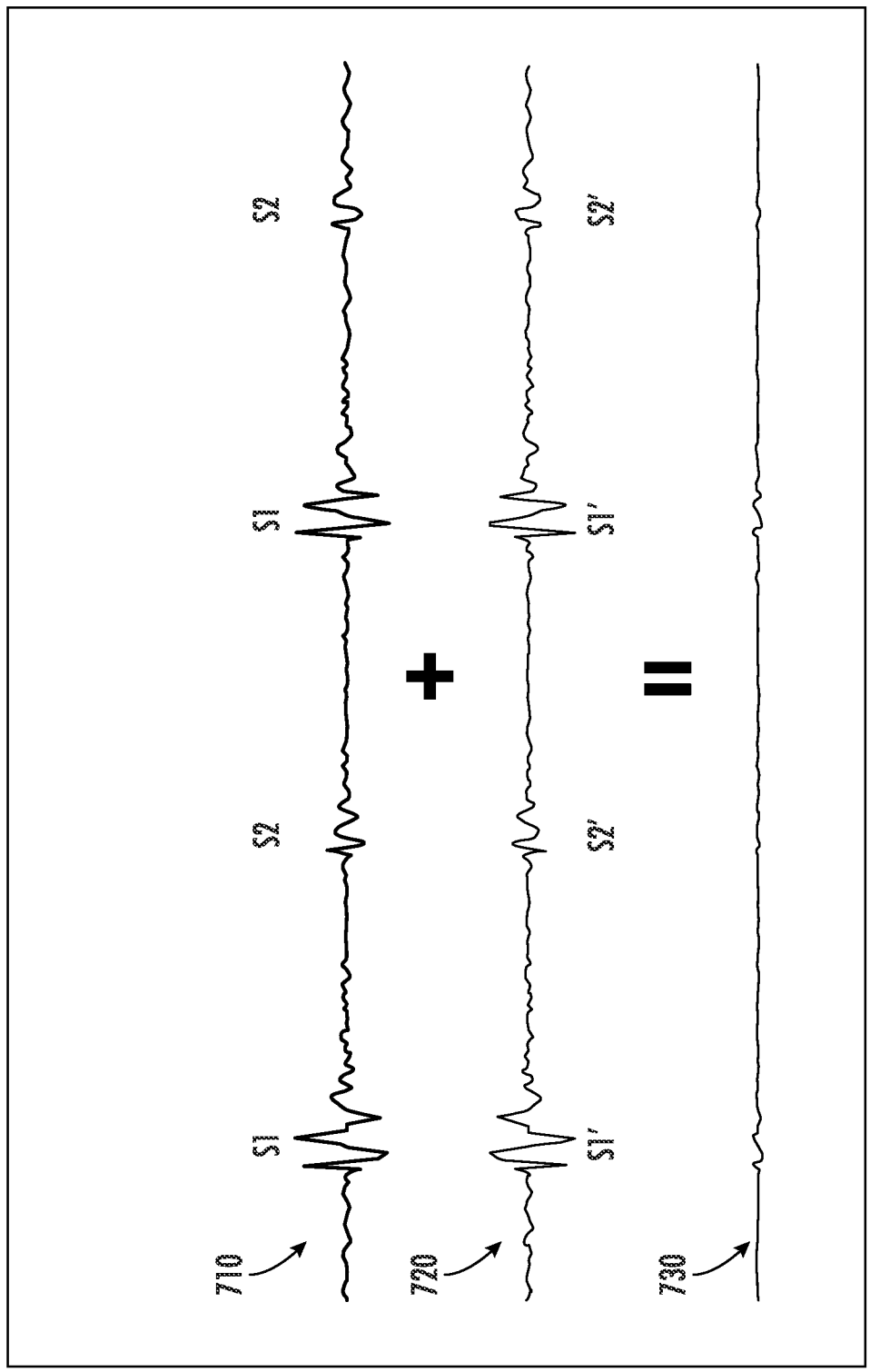
FIG. 7 shows vibration cancellation waveforms, in accordance with some embodiments.

FIG. 7 shows an example phonocardiogram of original vibrations 710 (S1-S2 waves) as detected by the sensors. Anti-vibration signals 720 (anti-vibration waves S1' and S2') are applied by actuators in response to the original vibrations. The combined signal 730 which results from original vibrations 710 added with anti-vibration signals 720 decreases the vibrations to a threshold that is acceptable to the patient or to a level at which the patient does not notice the vibrations. In some embodiments, as anti-vibration signals 720 travel through the chest cavity, the signals cancel or considerably reduce the vibration signal detected at the different nerve endings in the chest cavity. In other embodiments, anti-vibration signals 720 travel through the air to cancel noise signals from being heard by the patient.

In embodiments, learning algorithms of the present disclosure may analyze not only the vibrations that produce disturbances for the user, but also the patient's normal heart rhythms to improve accuracy of predicting future heart signals. For example, the algorithms may analyze the blood intake portion of each heart cycle to enable look-ahead estimation and to reduce processing latency. The algorithms may also learn indicators that precede speeding up or slowing down of the heart rate for an individual patient, which can also enable more accurate estimations and reduce processing latency.

Figure 8:
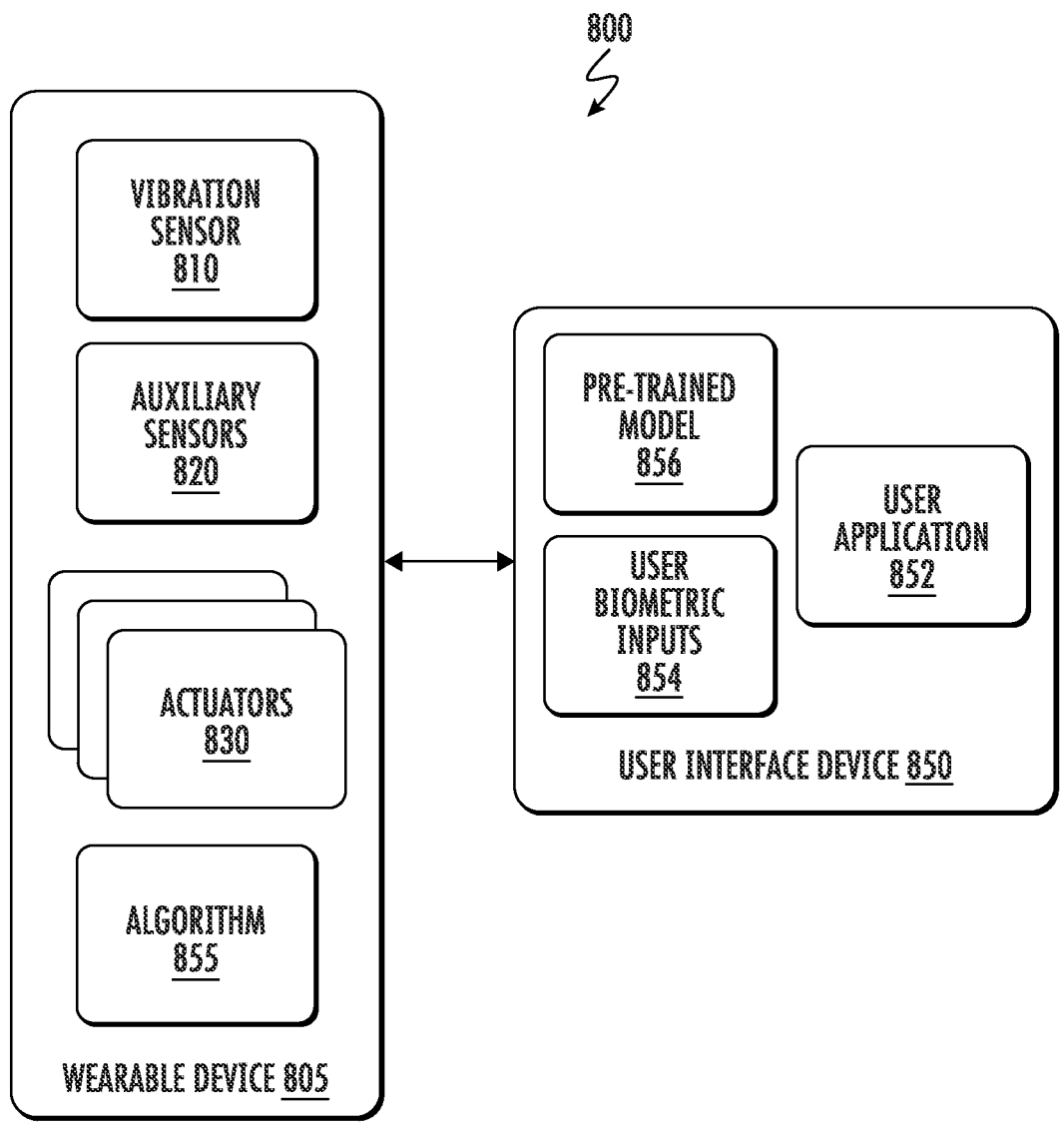
FIG. 8 is a block diagram of a vibration suppression system, in accordance with some embodiments.

FIG. 8 is a block diagram of an example system 800 for reducing artificial heart valve sounds perceived by a patient, in accordance with some embodiments. The system includes wearable device 805 (e.g., chest vest) and a user interface device 850. The user interface device 850 is an off-board device from the wearable device 805 and may be an electronic device such as a personal computer or mobile phone. The user interface device 850 has a user application 852 that allows the user (e.g., physician, technician or patient) to calibrate the wearable device 805 for the individual patient. The calibration or set-up session can be performed in, for example, a doctor's office or lab.

In some embodiments, the algorithm 855 receives an analog or digital representation of a signal associated with an artificial heart valve (e.g., an electrical signal, a vibration and/or an audible noise), determines an individual signal for each individual actuator that maximizes the attenuation levels of vibrations and noise felt by the patient (e.g., by producing a cancellation signal that is out of phase with the vibration or audible noise), and generates an analog or digital signal or instruction to control each actuator such that the actuator produces a noise or vibration that substantially attenuates the signal associated with the artificial heart valve. The amount of attenuation may be set according to the patient's tolerance of the noise and vibration disturbances, such as desiring to reduce the perceived sounds by at least 2 decibels (dBs), such as by at least 3 dBs, by at least 4 dBs or by at least 6 dBs. In some embodiments the algorithm can target to achieve at least a minimum amount of attenuation (e.g., at least 3 dBs or at least 4 dBs) regardless of the user's preferences.

In some embodiments, the algorithm implements a classical control strategy or modern strategy for active vibration control (AVC) that are known in the art. In some embodiments, the algorithm 855 implements a proportional-integral-derivative (PID) control algorithm. In some embodiments, the algorithm 855 implements a model predictive control (MPC) algorithm. In some embodiments, an electrical signal associated with the heart (e.g., ECG) is used to determine when signals associated with an artificial heart valve are being emitted and/or will be emitted. In some embodiments, the algorithm 855 includes a learning-adaptive predictive (LAP) algorithm 855 that uses artificial intelligence to learn vibration characteristics of the individual wearing the device, and then predict future vibrations based on those characteristics. In some embodiments, the LAP algorithm is a specially designed predictive algorithm that uses previously received analog or digital representation of the signal associated with the artificial heart valve to predict future characteristics of signals associated with the artificial heart valve, such as an amplitude, frequency content, and periodicity.

The user interface device 850 enables a user to input and store biometric inputs 854 into the system. During the setup session, which can be an initial setup for the patient or a periodic recalibration session, the user creates a profile which includes various user biometric inputs 854. The biometric inputs 854 can include information such as height, weight, sex, and age that can be used either as parameters for the algorithm 855 and/or to select a pre-trained model 856 via user interface device 850 to be used with a LAP algorithm of the algorithm 855. The pre-trained model 856 may be retrieved from a cloud processor (e.g., computing device 660 of FIG. 6) or from a selection built into the user application 852.

In embodiments that use a LAP algorithm as part of the algorithm 855, the next step is to run a calibration process on top of the pre-trained model 856 or initial LAP algorithm of the algorithm 855, taking input from the array of vibration sensors 810 on the wearable device 805.

The wearable device 805 (e.g., set-up vest 401) includes multiple locations for sensors 810 and actuators 830. In some embodiments, a computer database or algorithm may suggest an initial map of locations for the sensors 810 and actuators 830 on wearable device 805 based on the anatomy of the patient and their biometric inputs 854. The computer database or algorithm can also suggest the number and types of sensors 810 and actuators 830 to use. During the calibration phase, auxiliary measurements may be taken in addition to those from the wearable device 805, using auxiliary sensors 820. Auxiliary sensors 820 may include a heart rate sensor to measure heart rate and/or a blood pressure monitor to measure blood pressure. In some embodiments, a treadmill test can be performed, and calibration readings recorded during the test so that the LAP algorithm of the algorithm 855 learns how that patient's particular body structure (e.g., bone structure, bone density, fat percentage, distribution of fat within the chest, muscle mass) affects the vibrations generated by the artificial heart valve during physical activity. Readings can also be collected in a stationary mode, such as in different body positions that the patient sleeps in since the vibrations are often most bothersome to patients when sleeping. The calibration session may be used to find sensor locations where the strongest vibration signals are detected, especially when the patient is lying down. The calibration phase may also involve learning a threshold of vibration amplitudes that bother the patient, using subjective input from the patient.

Once the optimum locations of sensors and actuators has been determined from the calibration tests, the patient's customized vest is ordered based on the placements determined during the calibration phase. In the customized vest, the sensors in the plurality of the sensors and the actuators in the plurality of vibration-generating actuators are mounted in positions on the vest based at least in part on the measurements taken and other parameters gathered during the calibration phase. Similarly, the types and numbers of sensors and actuators utilized in the customized vest are based on the assessments made during the calibration phase.

The calibration phase may be performed multiple times during a patient's ongoing usage of the vest. For example, a calibration phase can be performed at an initial session for the patient using a setup vest. A calibration can also be performed for the patient's first use of their customized vest, to check that the vest is operating as planned. Calibrations may also be performed periodically such as every few months to further fine-tune the learning algorithm (in addition to adjustments made by the learning algorithm on an ongoing basis) and/or to see if changes in the patient's health or other conditions has affected how the vest is meeting the patient's needs. In some embodiments, measurements taken during the calibration phases may be used to determine or readjust the locations of the sensors and actuators across the vest, to replace sensors and/or actuators with different types of sensors and actuators, or to make software adjustments.

During normal usage, the chest vest senses the vibrations at multiple points around the wearer's chest. Based on the layout of the sensors' positions on the wearable device and based on the patient's bone and tissue structure, a personalized model is implemented per actuator per patient to ensure the best possible attenuation. In some embodiments, a LAP algorithm of the algorithm 855 makes predictions on future vibrations, such as the intensity, nature (e.g., waveform shape), frequency, and/or delay and/or time of occurrence of the next pulse, and programs the vibration-generating actuators 830 to generate the cancellation pulse. The sensors 810 continuously collect sensor readings, and the application continuously re-trains the algorithm 855 and outputs the best model to predict the next vibration pulse. In some embodiments, the continuous measurements by the sensors 810 are ongoing measurements that are made at a rate greater than that of phonocardiogram signals transmitted through bone and tissue and greater than a maximum frequency associated with the phonocardiogram signals. For example, for typical heart vibration signals that have a frequency spectrum of 1-2 kHz, the measurement algorithm of the present embodiments may utilize sampling rates that are at least twice that of a maximum frequency and/or frequency bandwidth of the frequency spectrum.

The LAP algorithm in the microcontroller monitors and measures vibrations and nearby sounds on an ongoing basis during usage, to try and predict the next vibrational pulse and the corresponding cancelation strategy for the actuators. The system may utilize pattern recognition algorithms and machine learning. The system is configured with low latency, with the microcontroller cycling at very fast speeds so that signals are processed faster than the periods of the frequencies of interest.

In some embodiments, a linear regression-based model may be used to generate the anti-vibration actuator waveform output needed to attenuate the vibration as felt at the patient's nerve endings. Some embodiments may utilize the Darmois-Skitovich Theorem which characterizes the Gaussian distribution by the independence of two linear forms from independent random variables. The Darmois-Skitovich Theorem has been used in the communications industry to effectively invert a communication channel without using pilot signals, and by radiologists to try to make intervening tissue noise essentially transparent.

In various embodiments a system for reducing vibrations perceived by a human due to an artificial heart valve includes a vest that is wearable around a torso of the human, a plurality of sensors mounted to the vest, a plurality of vibration-generating actuators mounted to the vest, and a controller. The plurality of sensors detects vibrations in the human generated by the artificial heart valve. The controller is operable to receive signals representing the detected vibrations from the plurality of sensors, and the controller is operable to produce anti-vibration signals that reduce, such as substantially attenuate, the detected vibrations. A first sensor of the plurality of sensors is located near a first vibration-generating actuator of the plurality of vibration-generating actuators to form a sensor/actuator set. In the sensor/actuator set, the anti-vibration signals generated by the controller for the first vibration-generating actuator correspond to the vibrations detected by the first sensor.

In some embodiments, the controller has an algorithm that makes predictions on future vibrations from the artificial heart valve in response to the detected vibrations from the plurality of sensors, and wherein the controller generates the anti-vibration signals for the plurality of vibration-generating actuators based on the predictions. In some embodiments, the plurality of sensors detects the vibrations on an ongoing basis, and the controller monitors and adaptively adjusts the algorithm based on the vibrations detected by the plurality of sensors. In some embodiments, the algorithm comprises parameters that are initially set according to a calibration phase, and the parameters comprise measurements of heart rate, blood pressure, or patient body structure. The patient body structure may include fat percentage, bone structure and bone density. The plurality of the sensors is mounted in positions on the vest based on the measurements from the calibration phase.

In some embodiments, the system includes a user interface device in communication with the controller. In some embodiments, the plurality of sensors comprises an accelerometer or a microphone. In some embodiments, the plurality of sensors comprises an acoustic sensor and a haptic vibration sensor. In some embodiments, the plurality of vibration-generating actuators comprises a haptic actuator or a non-haptic actuator. In some embodiments, the plurality of vibration-generating actuators comprises a speaker in a feedforward topology.

Figure 9:
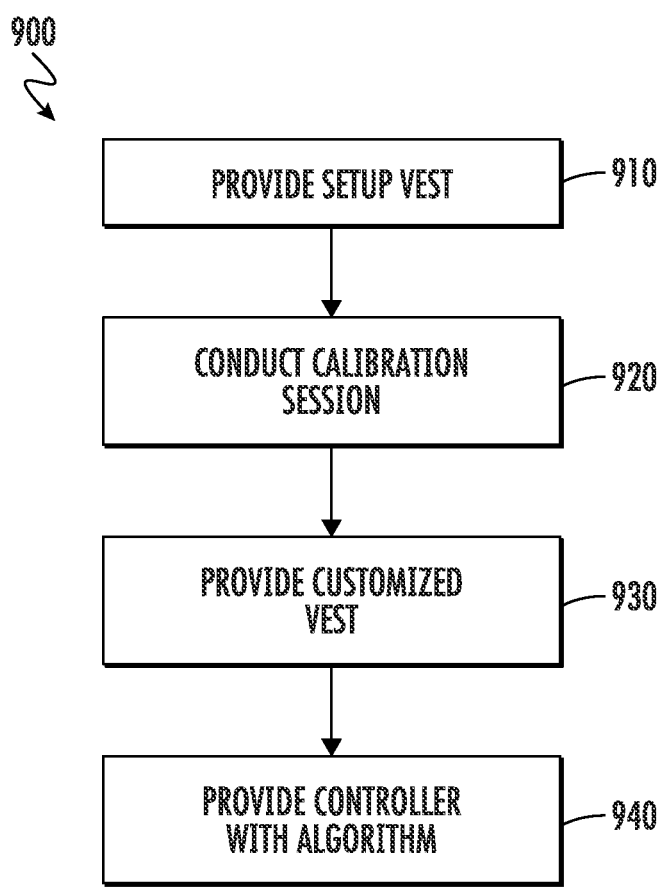
FIG. 9 is a flowchart of methods for reducing vibrations perceived by a human due to an artificial heart valve, in accordance with some embodiments.

FIG. 9 is a flowchart 900 representing methods for reducing vibrations perceived by a human due to an artificial heart valve. Step 910 involves providing a setup vest that is wearable around a torso of the human, the setup vest having a first plurality of sensors and a first plurality of vibration-generating actuators that are repositionable on the setup vest. In step 920, a calibration session is conducted to customize a placement of the first plurality of sensors and the first plurality of vibration-generating actuators on the setup vest. In step 930, a customized vest is provided to the human, the vest having a second plurality of sensors and a second plurality of vibration-generating actuators mounted on the vest according to the placement from the calibration session. The vest of step 930 is thus beneficially customized for the individual patient's anatomy and response to perceived vibrations. At least one sensor of the second plurality of sensors is located near at least one vibration-generating actuator of the second plurality of vibration-generating actuators to form a sensor/actuator set.

Embodiments also include step 940 of providing a controller operable to receive signals representing vibrations detected from the plurality of sensors, the vibrations being generated by the artificial heart valve. The controller is operable to produce anti-vibration signals that reduce, such as substantially attenuate, the detected vibrations. In the sensor/actuator set, the anti-vibration signals generated by the controller for the at least one vibration-generating actuator correspond to sensor readings from the at least one sensor. In some embodiments of the flowchart 900, the controller has an algorithm that makes predictions on future vibrations from the artificial heart valve in response to sensor readings produced by the second plurality of sensors. In some embodiments, the controller monitors and adaptively adjusts the algorithm based on the vibrations detected by the second plurality of sensors. In some embodiments, the system includes a user interface device in communication with the controller. In some embodiments, the plurality of sensors comprises an accelerometer or a microphone. In some embodiments, the plurality of sensors comprises an acoustic sensor and a haptic vibration sensor. In some embodiments, the plurality of vibration-generating actuators comprises a haptic actuator or a non-haptic actuator. In some embodiments, the plurality of vibration-generating actuators comprises a speaker in a feedforward topology.

Reference has been made in detail to embodiments of the disclosed invention, one or more examples of which have been illustrated in the accompanying figures. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. A system for reducing vibrations perceived by a human due to an artificial heart valve, the system comprising:
   a vest that is wearable around a torso of the human;
   a plurality of sensors mounted to the vest, wherein the plurality of sensors detects vibrations generated by the artificial heart valve;
   a plurality of vibration-generating actuators mounted to the vest; and
   a controller operable to receive signals of the detected vibrations from the plurality of sensors, and wherein the controller is operable to produce anti-vibration signals that reduce the detected vibrations;
   wherein a first sensor of the plurality of sensors is located near a first vibration-generating actuator of the plurality of vibration-generating actuators to form a sensor/actuator set; and wherein in the sensor/actuator set, the anti-vibration signals generated by the controller for the first vibration-generating actuator correspond to vibrations detected by the first sensor.

2. The system of claim 1, wherein the controller has an algorithm that makes predictions on future vibrations from the artificial heart valve in response to the detected vibrations from the plurality of sensors, and wherein the controller generates the anti-vibration signals for the plurality of vibration-generating actuators based on the predictions.

3. The system of claim 2, wherein:

the plurality of sensors detects the vibrations on an ongoing basis; and the controller monitors and adaptively adjusts the algorithm based on the vibrations detected by the plurality of sensors.

4. The system of claim 2, wherein:

the algorithm comprises parameters that are initially set according to a calibration phase; and the parameters comprise measurements of heart rate, blood pressure, or patient body structure.

5. The system of claim 4, wherein the patient body structure includes fat percentage, bone structure and bone density.

6. The system of claim 4, wherein the plurality of sensors are mounted in positions on the vest based on the measurements from the calibration phase.

7. The system of claim 1, further comprising a user interface device in communication with the controller.

8. The system of claim 1, wherein the plurality of sensors comprises an accelerometer or a microphone.

9. The system of claim 1, wherein the plurality of vibration-generating actuators comprises a haptic actuator.

10. The system of claim 1, wherein the plurality of vibration-generating actuators comprises a speaker in a feedforward topology.

11. The system of claim 1, wherein the plurality of sensors comprises an acoustic sensor and a haptic vibration sensor.

12. The system of claim 1, wherein the plurality of sensors and the plurality of vibration-generating actuators are releasably mounted to the vest, thereby enabling positions of the plurality of sensors and the plurality of vibration-generating actuators to be adjusted.

13. The system of claim 1, wherein the plurality of vibration-generating actuators comprises a feedforward microphone.

14. The system of claim 1, wherein the plurality of vibration-generating actuators comprises a non-haptic actuator.

* * * * *